United States Patent [19]

Krespan

[11] Patent Number: 4,766,248

[45] Date of Patent: Aug. 23, 1988

[54] β-SUBSTITUTED POLYFLUOROETHYL COMPOUNDS

[75] Inventor: Carl G. Krespan, Wilmington, Del.

[73] Assignee: E. I. Du Pont de Nemours and Company, Wilmington, Del.

[21] Appl. No.: 819,285

[22] Filed: Jan. 16, 1986

Related U.S. Application Data

[62] Division of Ser. No. 399,281, Jul. 19, 1982, Pat. No. 4,576,752.

[51] Int. Cl.$^4$ .................. C07C 147/02; C07C 147/06; C07C 149/16; C07C 149/273
[52] U.S. Cl. .......................................... 568/31; 568/43
[58] Field of Search ..................... 568/31, 43

[56] References Cited

U.S. PATENT DOCUMENTS

| | | | |
|---|---|---|---|
| 2,754,334 | 7/1956 | Bahner | 568/43 X |
| 2,988,537 | 6/1961 | Wiley | 260/67 |
| 3,091,643 | 5/1963 | Wiley | 260/595 |
| 3,513,203 | 5/1970 | Sianesi et al. | 260/594 |
| 3,683,027 | 8/1972 | Sianesi et al. | 260/594 |
| 4,156,696 | 5/1979 | Koshar | 568/31 |
| 4,160,780 | 7/1979 | Krespan | 260/513 F |
| 4,214,070 | 7/1980 | Krespan | 528/220 |
| 4,238,416 | 12/1980 | Tohzuka et al. | 568/384 |
| 4,337,211 | 6/1982 | Ezzell et al. | 260/456 F |
| 4,357,282 | 11/1982 | Anderson et al. | 568/43 X |
| 4,476,058 | 10/1984 | Millauer et al. | 260/458 F |
| 4,562,292 | 12/1985 | Hammock et al. | 568/43 |
| 4,576,752 | 3/1986 | Krespan | 568/31 X |
| 4,597,913 | 7/1986 | Kimoto et al. | 568/31 X |

FOREIGN PATENT DOCUMENTS

| | | |
|---|---|---|
| 41737 | 12/1981 | European Pat. Off. . |
| 2051831 | 1/1981 | United Kingdom . |
| 438636 | 8/1974 | U.S.S.R. . |

OTHER PUBLICATIONS (Chem. Abstr. vol. 82, 97627p, (1975), Kolenko, et al.
Glazkov et al., Izv. Akad. Nauk SSSR, Ser. Khim, No. 4, p. 918, (Apr. 1976).

*Primary Examiner*—Joseph Paul Brust
*Attorney, Agent, or Firm*—James A. Costello

[57] ABSTRACT

β-Substituted polyfluoroethyl compounds, process for the preparation thereof, copolymers thereof, compound intermediates, and process therefor. The copolymers are useful as ion exchange resins or structural foams.

14 Claims, No Drawings

β-SUBSTITUTED POLYFLUOROETHYL COMPOUNDS

This is a division of application Ser. No. 399,281, filed July 19, 1982, now U.S. Pat. No. 4,576,752.

FIELD OF THE INVENTION

This invention relates to β-substituted polyfluoroethyl compounds, a process for their preparation, polymers prepared from them, compound intermediates, and a process for preparing the intermediates.

BACKGROUND INFORMATION

U.S. Pat. No. 2,988,537 discloses the following reaction:

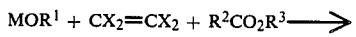

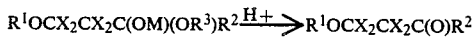

wherein X is halogen, M is alkali metal and $R^1$ and $R^3$ alkyl or fluorinated alkyl having up to 18 carbon atoms; $R^2$ is defined as $R_1$ but limited to 12 carbon atoms.

U.S. Pat. No. 3,091,643 discloses the following reaction:

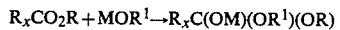

wherein $R_x$ is a monovalent polyfluoroperhalocarbyl or ω-hydroperfluoroperhalocarbyl radical; R and $R^1$ are hydrocarbyl having up to eight carbon atoms and M is alkali metal.

U.S. Pat. No. 4,238,416 discloses conversion of fluorinated epoxides,

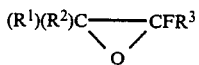

to carbonyl compounds such as $R_FC(O)CF_3$, $R_FC(O)CF_2R_F$ and $(R_F)_2CFC(O)R_F$ wherein $R_F$ is perfluoroalkyl or ω-hydroperfluoroalkyl and $R^1$-$R^3$ are —$R_F$ or —F.

U.S. Pat. Nos. 3,513,203 and 3,683,027 disclose preparation of polyfluorinated ketones by photochemical combination of liquid $C_3F_6$ with oxygen and heating the resulting perfluoropolyethers having acid fluoride end groups.

U.S. Pat. Nos. 4,214,070 and 4,160,780 disclose preparation of ketoperfluorosulfonic acids having the formula $R_F{}^1CF_2C(O)CF(R_F)SO_2H$ and esters thereof, wherein $R^1F$ and $R_F$ are —F or $C_{1-4}$ perfluoroalkyl, and their use as comonomers.

U.S.S.R. Pat. No. 438,636 discloses compounds having the formula $ROCF_2CF_2C(O)CF(CF_3)OR$, wherein R is a fluorinated aliphatic, alicyclic or aromatic group, which are prepared from perfluoro-β-substituted propionate salts.

U.K. Patent Application No. 2,051,831 discloses the fluoroketone, $RSCF_2CF_2C(O)CF_2CF_2SR$, where R is $C_{1-10}$ alkyl (embracing $R^1SCF_2CF_2Z$ when Z is —C(O)$R_FX^1$ and $R_FX^1$ is —$CF_2CF_2SR^1$) and also discloses acyl fluorides and vinyl ethers having the respective formulas $RZ(CF_2)_{3-5}[OCF(CF_3)CF_2]_{0-5}OCF(CF_3)COF$ and $RZ(CF_2)_{3-5}[OCF(CF_3)CF_2)_{0-5}OCF=CF_2$ wherein Z is —S— or —$SO_2$— and R is $C_{1-10}$ alkyl.

European Patent Application 41,736 discloses compounds of the formula, $Y(CF_2)_a(CFR_F)_bC(O)R'_F$ wherein Y includes —$SO_2R$, —$SO_2F$, —$SO_2Cl$; R is H, alkyl or aryl; a and b are, independently, 0 or integers, and $R_F$ and $R'_F$ are, independently, F, Cl, perfluoroalkyl or fluorochloroalkyl. This formula embraces $XCF_2CFYZ$ when X is —$SO_2R^1$, —$SO_2F$ or —$SO_2Cl$, Y is F or Cl, Z is —$C(O)R_FX^1$ and $R_FX^1$ is perfluoroalkyl. An enabling process for preparing the compounds is not provided.

European Patent Applications 41,736 and 41,737 disclose compounds of the formula $Y(CF_2)_a(CFR_F)_bCFR'_FO[CF(CF_2X)CF_2O]_nCF(CF_2X')COF$ and $Y(CF_2)_a(CFR_F)_bCFR'_FO[CF(CF_2X)CF_2O]_nCF=CF_2$ where Y is an acid group or a group convertible to an acid group; a and b, individually, are 0 or an integer; $R_f$ and $R'_f$ are each independently selected from F, Cl, perfluoroalkyl and fluorochloroalkyl; X is F, Cl or Br; and X' is Cl or Br. These compounds are prepared from an intermediate for which enablement is not provided. These formulae embrace $XCF_2CFYZ$ when X is —$SO_2R^1$, —$SO_2F$ or —$SO_2Cl$; Y is F or Cl, Z is —$CF(R_FX^1)OQ_nCF(CF_3)COF$ or —$CF(R_FX^1)OQ_nCF=CF_2$ and $R_FX'$ is perfluoroalkyl.

Kalenko et al., Zh. Vses. Khim. O-va, Volume 19, No. 6, 707 (1974) [Chem. Abstr., Volume 82, 97627p (1975)], disclose the following reaction:

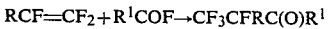

wherein R is —$CF_3$, —$OCF_3$ or —$O(CF_2)_2CF$ and $R^1$ is —$CF_2OCF_3$, —$CF_2CF_2OCF_3$ or $(CF_2CF_2)_{(1-3)}H$.

Glazkov et al., Izv. Akad. Nauk SSSR, Ser. Khim, No. 4, page 918 (April 1976), disclose preparation of perfluoroether ketones by heating perfluoroalkylvinyl ethers.

European Patent Application No. 47,945 discloses fluorinated keto sulfonyl fluorides $R_FC(O)(CF_2)_nSO_2F$ wherein $R_F$ is F or $C_{1-10}$ perfluoroalkyl and n is 0 or an integer of 1 to 7.

SUMMARY AND DETAILS OF THE INVENTION

This invention resides in a process for the preparation of a β-substituted polyfluoroethyl compound, in the polyfluoroethyl compound and an intermediate, in a process for the preparation of the intermediate and in copolymers of the polyfluoroethyl compound with fluorinated monoolefins.

In the process of the invention a polyfluoroolefin, $CF_2=CFY$, is mixed and reacted with a metal salt, $MX^2$; and a fluoroester, $X^1R_FCO_2R$, and the product intermediate is converted to the β-substituted polyfluoroethyl compound. In said process, $X^1$ is —F, —$SR^1$, —$SO_2R^1$, —$CO_2R$, —$N_3$ or —$OR^2$;

$X^2$ is —$SR^1$, —$N_3$, —$OC_6F_5$ or —$OC_6H_5$ which may be optionally alkylated;

R is —$CH_2CF_3$, —$CH_2(CH_2CF_2)_{(1-6)}H$, —$C_6H_5$ or $C_{1-3}$ alkyl;

$R^1$ is $C_{1-10}$ alkyl, $C_{6-10}$ aryl or $C_{6-10}$ aralkyl;

M is alkali metal;

Y is —F, —Cl or —$OR_F{}^1$;

$R^2$ is —$CH_3$, —$C_2H_5$ or —$C_6H_5$;

$R_F$ is —$CF_2$— or $C_{2-8}$ perfluoralkylene, optionally containing one in-chain ether oxygen bond, or two in-chain ether oxygen bonds separated by at least two carbon atoms; and $R_F^1$ is $C_{1-4}$ perfluoroalkyl.

The intermediate is the compound having the formula $XCF_2CFYC(OM)(OR)R_FX^4$ wherein $X^4$ is $X^1$ or $-C(OR)(OM)CFYCF_2X$ where X is $-SR^1$, $-N_3$, $OC_6F_5$, optionally alkylated $-OC_6H_5$, $SO_2R^1$, $-SO_2F$, or $-SO_2Cl$, and $X^1$, Y, M, R and $R_F$ are as defined above. The intermediate wherein $X^4$ is $-C(OR)(OM)$-$CFYCF_2X$ arises only when a diester reactant is employed.

The β-substituted polyfluoroethyl compound has the formula $XCF_2CFYZ$ wherein:

X is $-SR^1$, $-N_3$, $-OC_6F_5$, optionally alkylated $-OC_6H_5$, $-SO_2R^1$, $-SO_2F$, or $-SO_2Cl$;

Y is $-F$, $-Cl$ or $-OR_F^1$;

Z is selected from $-C(O)R_FX^1$, $-CF(R_FX^1)OQ_nCF(CF_3)COF$, $-CF(R_FX^1)OQ_nCF(CF_3)CO_2M^1$, $-CF(R_FX^1)OQ_nCF=CF_2$, $-CF(R_FX^1)OQ_mCF_2CF=CF_2$, and $Z^1R_FZ^1CFYCF_2X$;

Q is $-CF(CF_3)CF_2O-$;

$M^1$ is an alkali metal, alkaline earth metal or ammonium;

n is 0-6;

m is 0-7;

$Z^1$ is $-C(O)-$, $-CF(OQ_nCF(CF_3)COF)-$, $-CF(OQ_nCF(CF_3)CO_2M^1)-$, $-CF(OQ_nCF=CF_2)-$, or $-CF(OQ_mCF_2CF=CF_2)-$; and $X^1$, Y, $R^1$, $R_F$, $R_F^1$ are as defined above; except that when X is $-SR^1$, Y is $-F$, Z is $-C(O)R_FX^1$ and $R_F$ is $-CF_2CF_2-$, $X^1$ cannot be $-SR^1$.

Preferably: X is $-SR^1$, $-SO_2R^1$, $-N_3$, $-OC_6F_5$ or $-OC_6H_5$; Y is $-F$ or $-OCF_3$; $X^1$ is $-F$, $-N_3$, $-CO_2R$ or $-OCH_3$; R is $-CH_3$, $-CH_2CF_3$ or $-C_6H_5$; $R^1$ is $-CH_3$, $-C_2H_5$ or $-C_6H_5$; $R_F$ is $-CF_2-$, $-CF_2CF_2-$ or $-CF_2OCF_2-$; and Z is $-C(O)R_FX$ or $-C(O)R_FC(O)CFYCF_2X$.

The copolymers of the invention have repeat units of the formula:

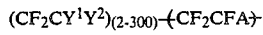

wherein:

$Y^1$ is $-F$ or $-H$;

$Y^2$ is $-F$, $-H$, $-Cl$, $-R_F^1$ or $-OR_F^1$; and

A is $-CF_2Q_mOCF(R_FX^1)X^3$, $-Q_nOCF(R_FX^1)X^3$, $-CF_2Q_mOCF(X^3)R_FCF(X^3)OQ_mCF_2CF=CF_2$, or $-Q_nOCF(X^3)R_FCF(X^3)OQ_nCF=CF_2$, wherein $X^3$ is $(CFYCF_2X)$ and X, $X^1$, Y, Q, $R_F$, $R_F^1$, n and m are as defined above.

In the process for preparing the intermediate compound, the reactants can be prepared by known techniques and mixed in any order. The relative amounts of the reactants are not critical. Typically, they are approximately equimolar. A useful temperature is about 20° to 100° C., the preferred temperature being about −10° to 50° C. When R is $C_{1-3}$ alkyl, the temperature is preferably about −10° to 15° C. Reaction time can vary broadly from a few minutes to about a day, the optimum time depending to a large extent upon the reaction temperature. Reaction pressure is not critical. Pressure of about 25 to 500 psi (170 to 3450 kPa) is preferred. The reactants are preferably mixed in a polar aprotic solvent such as dimethyl sulfoxide (DMSO), hexamethylphosphoramide, acetonitrile, tetramethylene sulfone, tetrahydrofuran (THF), tetraglyme, diglyme and dimethylformamide (DMF).

The β-substituted polyfluoroethyl compound of the invention, $XCF_2CFYZ$, wherein X is $SR^1$; $-N_3$, $-OC_6F_5$ or $OC_6H_5$ which may be optionally alkylated, and Z is $-C(O)R_FX^1$ or $Z^1R_FZ^1CFYCF_2X$, and $Z^1$ is $-C(O)-$, are prepared by treating the intermediate, which need not be isolated from the reaction mixture, with a mineral acid. The acid can be anhydrous, in which case an amount approximately equivalent to the amount of the product is typically added to the reaction mixture, followed by fractionation to collect the ketone. The acid can also be aqueous in which case an excess amount is typically added, followed by extraction with ether, concentration of the extracts, dehydration of the ketone hydrate with, for example, $P_2O_5$, and fractionation to collect the polyfluoroethyl compound.

The functional group $-SR^1$ can be converted to $-SO_2R^1$, $-SO_2F$ or $-SO_2Cl$, by known techniques as described, for example, by Ward in J. Org. Chem., Volume 30, 3009 (1965).

The β-substituted polyfluoroethyl compound in which Z is $-C(O)R_FX^1$ or $-Z^1R_FZ^1CFYCF_2X$ and $Z^1$ is $-C(O)-$ can be reacted with hexafluoropropene oxide (HFPO) to form the HFPO adduct or diadduct, that is, the polyfluoroethyl compound in which Z is $-CF(R_FX^1)OQ_nCF(CF_3)COF$ or $-Z^1R_FZ^1$-$CFYCF_2X$ and $Z^1$ is $-CF(OQ_nCF(CF_3)COF)-$.

The perfluoroallyl ether, that is, the polyfluoroethyl compound in which Z is $-CF(R_FX^1)OQ_mCF_2CF=CF_2$ or $-Z^1R_FZ^1CFYCF_2X$ and $Z^1$ is $-CF(OQ_mCF_2CF=CF_2)-$ can be prepared by reacting the acid fluoride, or an HFPO adduct thereof, with perfluoroallylfluorosulfate or perfluoroallylchloride in the presence of fluoride ions as described, for example, in U.S. Pat. Nos. 4,273,728; 4,273,729, and 4,275,225.

The perfluorovinyl ether, that is, the polyfluoroethyl compound in which Z is $-CF(R_FX^1)OQ_nCF=CF_2$ or $-Z^1R_FZ^1CFYCF_2X$ and $Z^1$ and $-CF(OQ_nCF=CF_2)-$ can be prepared by pyrolyzing the acid fluoride containing at least one Q group, and preferably at least two such groups, optionally in an aprotic solvent, in the presence of a carbonate, phosphate, sulfite or sulfate salt of an alkali or alkaline earth metal, preferably sodium carbonate or trisodium phosphate.

The perfluorovinyl ether described above wherein Z is $-CF(R_FX^1)OQ_nCF=CF_2$ or $-Z^1R_FZ^1CFYCF_2X$ and $Z^1$ is $-CF(OQ_nCF=CF_2)-$, can also be prepared by pyrolyzing, at reduced pressure, the derivative wherein Z is $-CF(R_FX^1)OQ_nCF(CF_3)CO_2M^1$ or $-Z^1R_FZ^1CFYCF_2X$ and $Z^1$ is $-CF(OQ_nCF(CF_3)CO_2M^1)-$, in the absence of solvents or added salts (as in Example 12B). The latter derivatives are prepared by alkaline hydrolysis of the corresponding acyl fluorides.

The β-substituted polyfluoroethyl compounds of the invention which contain the fluorinated allyl or vinyl ether-containing groups are copolymerizable with fluorinated monoolefins such as, for example, tetrafluoroethylene, trifluoroethylene, chlorotrifluoroethylene, vinylidene fluoride and mixtures of tetrafluoroethylene with hexafluoropropene and/or perfluoroalkyl vinyl ethers as described, for example, in U.S. Pat. Nos. 4,273,728; 4,273,729; and 4,275,225.

The copolymers of the invention, which are moldable into shaped articles, such as films, have pendant functional groups, X or $X^1$, which confer special utility. When X is $-SO_2R$, $-SO_2F$, or $-SO_2Cl$ the copolymers have ion-exchange properties after hydrolysis, the $-SO_2R$ groups requiring conversion to sulfonates or carboxylates as taught by Ward in J. Org. Chem., Volume 30, 3009 (1965). Use of fluoropolymers having a pendant sulfonate group as ion-exchange membranes is disclosed in U.S. Pat. No. 4,176,215, and as electrolysis cell diaphragm materials in U.S. Pat. Nos. 4,164,463 and 3,853,720.

Copolymers having pendant —$N_3$ groups can be converted into chemically stable, structural foams by heating to a temperature at which $N_2$ is released, the gas serving as a blowing agent.

Such copolymers can also be converted to useful cyano-substituted copolymers by reaction of the pendant —$CF_2N_3$ groups with a tertiary phosphine such as triphenylphosphine. The cyano-substituents provide cure sites permitting conversion of the copolymers to fluoroelastomers as described in U.S. Pat. No. 4,281,092. Copolymers having pendant —$CO_6F_5$ groups may also be cured to fluoroelastomers as described in U.S. Pat. No. 3,467,638. Copolymers having pendant —$CF_2OC_6H_5$ groups may be hydrolyzed in strong aqueous acids to provide pendant —$CO_2H$ groups which, on treatment with aqueous alkali, are converted to carboxylate groups having ion-exchange properties.

EXAMPLES

In the following Examples, which are illustrative of the invention, all parts and percentages are by weight and all temperatures are in degrees Celsius. Table 1 summarizes the various compounds made in the Examples.

ethylene was shaken in a 400-mL tube at about 30° to 35° for 8 hours during which time the pressure droppd from greater than 400 psi (675 kPa) to about 130 psi (220 kPa). The temperature was increased to about 50° at which the pressure was about 140 psi (235 kPa), for two more hours after which the pressure was about 135 psi (230 kPa). The reaction mixture was poured into a solution of 200 mL of concentrated HCl in 1 liter (L) of ice water. A lower layer was washed with a solution of 50 mL of concentrated HCl in 500 mL of water and then with 500 mL of water to give 135.3 g of oil. The oil was stirred overnight with 258 g (1.23 mol) of trifluoroacetic anhydride in an attempt to remove all the water. Fractionation yielded 91 g of a mixture containing both 4-phenoxyheptafluorobutanone-2 and its hydrate, bp 25° (10 mm, 1.3 kPa) −42° (1 mm, 0.1 kPa). This crude product was dissolved in 50 mL of $CFCl_2CF_2Cl$ and stirred with 30 g. The $CFCl_2CF_2Cl$ solution was decanted and the product was stirred with an additional 10 g of $P_2O_5$. The organic layer was decanted and distilled to afford 54.2 g (47%) of 4-phenoxyheptafluorobutanone-2, bp 70°–74° (40 mm, 5.3 kPa). IR ($CFl_4$): 3080 (arom CH), 1790 (C=O), 1600, 1590, and 1490 (arom C=C), and 1250–1100 cm$^{-1}$ (CF, C—O). NMR ($CCl_4$): $^1H$ 7.23 ppm (m, arom CH), $^{19}F$ −75.4 (t of t, $J_{FF}$ 8.3, 2.5 Hz, 3F, $CF_3$), −84.6 (t of q, $J_{FF}$ 4.7, 2.5 Hz, 2F, $OCF_2$), and −118.1 ppm (q of t, $J_{FF}$ 8.3, 4.7 Hz, 2F, $CF_2C$=O).

TABLE 1

| | (1) $XCF_2CFYZ$ | | | (2) $XCF_2CFYC(OM)(OR)R_FX^4$ | | |
|---|---|---|---|---|---|---|
| Example | X | Y | Z | M | R | $R_FX^4$ |
| 1 | $C_6H_5O$ | F | $COCF_3$ | Na | $C_6H_5$ | $CF_3$ |
| 2 | $C_6H_5O$ | $OCF_3$ | $COCF_3$ | Na | $C_6H_5$ | $CF_3$ |
| 3 | $CH_3S$ | F | $COCF_3$ | Na | $CH_2CF_3$ | $CF_3$ |
| 4 | $CH_3S$ | F | $CO(CF_2)_2OCH_3$ | Na | $CH_3$ | $CF_2CF_2OCH_3$ |
| 5 | $N_3$ | F | — | Na | $CH_2CF_3$ | $CF_3$ |
| 6 | $N_3$ | F | $COCF_3$ | — | — | — |
| 7 | $N_3$ | F | $COC_2F_5$ | — | — | — |
| 8 | $N_3$ | F | $CO(CF_2)_2OCH_3$ | — | — | — |
| 9 | $N_3$ | F | $Z^1R_FZ^1CFYCF_2X$ $Z^1 = $ —CO— $R_F = $ —$CF_2OCF_2$— | Na | $CH_2CF_3$ | $CF_2OCF_2C(ONa)$— $(OCH_2CF_3)CF_2CF_2N_3$ |
| 10 | $N_3$ | F | $CO(CF_2)_2N_3$ | Na | $CH_2CF_3$ | $CF_2CF_2N_3$ |
| 11 | $CH_3SO_2$ | F | $COCF_3$ | — | — | — |
| 12 | $N_3$ | F | $CF(CF_3)OQCF(CF_3)COF$, $CF(CF_3)OQCF(CF_3)CO_2Na$, $CF(CF_3)OQCF$=$CF_2$ and copolymer with TFE | — | — | — |
| 13 | $CH_3SO_2$ | F | $CF(CF_3)OCF_2CF$=$CF_2$ | — | — | — |

EXAMPLE 1

4-Phenoxyheptafluorobutanone-2

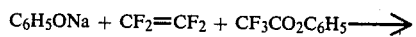

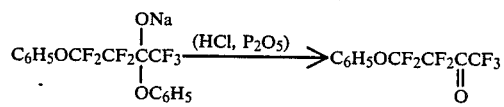

Phenyl trifluoroacetate, bp 53°–55° (20 mm, 2.7 kPa) was prepared in 95% yield as described by Hudlicky in "Chemistry of Organic Fluorine Compounds," Wiley, New York, 1976, p. 708 Sodium phenoxide was prepared as described by N. Kornblum and A. P. Lurie, J. Am. Chem. Soc., Volume 81, 2705 (1959).

A mixture of 46.4 g (0.40 mol) of anhydrous sodium phenoxide, 90.6 g (0.48 mol) of phenyl trifluoroacetate, 150 mL of DMSO, and 50 g (0.50 mol) of tetrafluoro- Anal. Calcd for $C_{10}H_5F_7O_2$: C, 41.40; H, 1.74. Found: C, 41.71; H, 1.90.

EXAMPLE 2

4-Phenoxy-3-trifluoromethoxyhexafluorobutanone-2

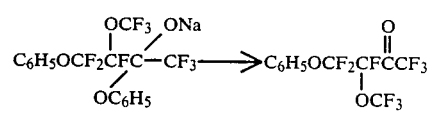

A 400-mL tube was charged with 46.4 g (0.40 mol) of sodium phenoxide, 90.6 g (0.48 mol) of phenyl trifluoroacetate, 150 mL of DMSO, and 83 g (0.50 mol) of perfluoro (methyl vinyl ether). The tube was shaken at 25° for 8 h, then at 50° for 2 h. The reaction mixture was poured into a solution of 200 mL of concentrated HCl in 1 L of ice water, and a product layer was extracted with a solution of 50 mL of concentrated HCl in 500 mL of water. The aqueous layer was extracted twice with ether, and the ether extracts were evaporated to give additional crude product. The combined products were diluted with benzene, and water (12 mL) was azeotroped off. The clear benzene solution was stirred with 142 g (1.0 mol) of $P_2O_5$ until an exotherm had subsided. The solution was left to stand overnight, and then heated to reflux. The benzene solution was decanted and distilled to afford 47.2 g (33%) of 4-phenoxy-3-trifluoromethoxyhexafluorobutanone-2, bp 61°-70° (5 mm, 0.6 kPa). A fraction containing only minor impurity by GC was analyzed. IR ($CCl_4$: 3080 (arom. CH), 1790 (C=O), 1595 and 1495 (arom. C=C), and 1300–1100 cm$^{-1}$ (CF, C—O). NMR ($CCl_4$): $^1H$ 7.2 ppm (m,, arom. CH); $^{19}F$ −55.0 (d of q, $J_{FF}$ 9.2, 2.6 Hz, 3F, $OCF_3$), −74.7 (d of sextets, $J_{FF}$ 14.0, 3 Hz, 3F, $CF_3C$=O), and −138.2 ppm (q of p, $J_{FF}$ 14.0, 9 Hz, 1F, CF) with an AB for $CF_2O$ at −7652 and −7790 Hz (q, $J_{FF}$ 3.4 Hz, 1F) and −7885 −8022 Hz (d of q, $J_{FF}$ 9.1, 3.4 Hz, 1F).

Anal. Calcd for $C_{11}H_5F_9O_3$: C, 37.09, H, 1.42; F, 48.01. Found: C, 37.00; H, 135; F, 48.18.

EXAMPLE 3

4-Methylthioheptafluorobutanone-2

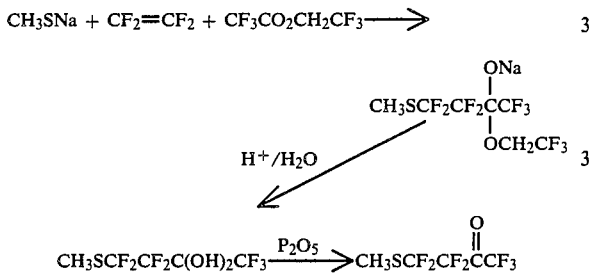

A suspension of 24.0 g (0.50 mol) of 50% NaH/mineral oil in 150 mL of tetrahydrofuran was treated with 2 g (0.01 mol) of trifluoroethyl trifluoroacetate to serve as catalyst for salt formation. The mixture was then stirred at 25°-40° while 24.0 g (0.50 mol) of methyl meercaptan was distilled in. The mixture was stirred until evolution of gas through a −80° condenser had ceased (2 h). The mixture was cooled in an ice-water bath while 117.6 g (0.60 mol) of trifluoroethyl trifluoroacetate was added. A 400-mL tube charged with the above mixture and 50 g (0.50 mol) of tetrafluoroethylene was agitated for 6 h while the temperature rose to 36°, then for 1 h at 50°. Volatiles were removed from the reaction mixture under reduced pressure, and the residue was treated and stirred successively with 50 mL of ether, 50 g of concentrated HCl, and 21.0 g of NaHCO$_3$. When gas evolution ceased after the last addition, the mixture was filtered and the moist solids were rinsed with ether. Fractionation of the combined filtrates afforded 109.8 g of crude 4-methylthioheptafluorobutanone-2 hydrate containing some tetrahydrofuran, bp 65°-68° (90 mm, 12.0 kPa).

The crude product was stirred for 6 h with 30 mL of $CFCl_2CF_2Cl$ and 100 g of $P_2O_5$. Then volatiles were transferred under vacuum at 25° and fractionated. The first product fraction, 56.3 g of crude 4-methylthioheptafluorobutanone-2, bp 86°-94°, was redistilled to give 40.2 g (33%) of pure 4-methylthioheptafluorobutanone-2, bp 57°-60° (200 mm, 26.6 kPa). IR ($CCl_4$): 3010, 2940, and 2850 (sat'd CH); 1785 (C=O), 1250–1100 cm$^{-1}$ (CF). NMR ($CCl_4$): $^1H$ 2.37 ppm (t of t, $J_{FF}$ 1.3, 0.9 Hz, $CH_3S$); $^{19}F$ −75.6 (t of t, $J_{FF}$ 8.4, 4.2 Hz, 3F, $CF_3$), −91.7 (t of q of m, $J_{FF}$ 5.8, 4.2 Hz, 2F, $CF_2S$), and −116.6 ppm (q of t of m, $J_{FF}$ 8.4, 5.8 Hz, 2F, $CF_2$). Mass spec (E.I): m/e 243.9794, M$^+$ (calcd for $C_5H_3F_7OS$, 243.973); 224.9873, M$^+$—F (calcd 224.9808); 205.9938, M$^+$—2F (calcd 205.9825); 196.9808, M$^+$—CH$_3$S (calcd 196.9837).

Anal. Calcd for $C_5H_3F_7OS$: C, 24.60; H, 1.24. Found: C, 24.97; H, 1.48.

Further distillation of the material which had been treated with $P_2O_5$ gave 16.2 g (10%) of 4-methylthioheptafluorobutanone-2 hydrate° 5/6 tetrahydrofuran, bp 70° (100 mm, 13.3 kPa). IR (neat): 3100 (broad, H-bonded OH), 2980 and 2880 (sat'd CH), and 1300–1100 cm$^{-1}$ (CF, C—O). NMR ($CCl_4$): $^1H$ 5.58 (s, 2H, OH) and 2.36 ppm (s, 3H, $CH_3S$) with bands for 5/6 THF at 3.78 ($CH_2O$) and 1.89 ppm ($CH_2$).

Anal. Calcd for $C_5H_5F_7O_2S_5/6C_4H_8$: C, 3.106; H, 3.65. Found: C, 31.11; H, 3.81.

Example 4

1-methoxy-5-methylthiooctafluoropentanone-3

$CH_3SNa + CF_2=CF_2 + CH_3OCF_2CF_2CO_2CH_3 \longrightarrow$ $$CH_3SCF_2CF_2\underset{\underset{OCH_3}{|}}{\overset{\overset{}{|}}{C}}CF_2CF_2OCH_3 \xrightarrow{H^+}$$

$$CH_3SCF_2CF_2\overset{O}{\overset{\|}{C}}CF_2CF_2OCH_3$$

A mixture of 24 g (0.50 mol) of 50% NaH/mineral oil and 150 mL of tetrahydrofuran was stirred under a −80° condenser while 24.0 g (0.50 mol) of methyl mercaptan was distilled in. Gas evolution subsided quickly but resumed upon addition of 2.0 g (0.01 mol) of trifluoroethyl trifluoroacetate. After stirring overnight, the mixture was cooled to 0° and added to a 400-mL tube along with 114.0 g (0.60 mol) of cold methyl 3-methoxytetrafluoropropionate. The mixture was agitated at 10° while 50 g (0.50 mol) of tetrafluoroethylene was injected. An exotherm to 26° was followed by a reaction period of 20 h at 10°.

The reaction mixture was acidified with 50 g (0.5 mol) of concentrated HCl and warmed to 30° (40 mm, 5.3 kPa) to remove volatiles. A residual oil and solid mixture was extracted with 2×200 mL ether, and the extracts were stirred with excess NaHCO$_3$ until gas evolution ceased. The ether solution was then dried over CaSO$_4$, extracted with ether and distilled to afford 41.0 g (27%) of 1-methoxy-5-methylthiooctafluoropentanone-3, bp 65°-66° (6 mm, 0.8 kPa). IR (neat): 3010, 2960 and 2860 (sat'd CH), 1775 (C=O), and 1250–110 cm$^{-1}$ (CF, C—O), Mass spec. (E.I.): m/e 305.9950, M$^+$ (calcd for $C_7H_6F_8O_2S$, 305.9960); 286,9960, M$^+$—F (calcd 286.9977); 159.0078, $CH_3OCF_2CF_2CO$ (calcd 159.0069); 146.9890, $CH_3SCF_2CF_2^+$ (calcd 146.9891); 131.0096, $CH_3OCF_2CF_2^+$ (calcd 131.0119).

EXAMPLE 5

6-Azido-4-hydroxy-4-trifluoromethyl-1,1,1,5,5,6,6-heptafluoro-3-oxahexane, sodium salt

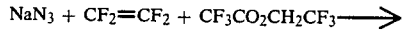

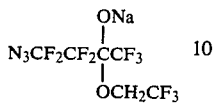

A 400-mL tube was charged with 26.0 g (0.40 mol) of sodium azide, 98.8 g (0.50 mol) of trifluoroethyl trifluoroacetate, 150 mL of DMSO, and 40 g (0.40 mol) of tetrafluoroethylene. The tube was shaken at ambient temperature (about 30°) for 4 h, then at 50° for 4 h. Pressure readings indicated that the reaction was substantially complete at 30°.

To demonstrate that the product was $N_3CF_2CF_2C(ONa)(OCH_2CF_3)CF_3$, the reaction mixture was stirred overnight with 56.7 g (0.45 mol) of dimethyl sulfate, then heated to 40° (0.5 mm, 0.1 kPa) to remove volatiles. Fractionation of the volatiles gave 101.4 g (72%) of 6-azido-4-methoxy-4-trifluoromethyl-1,1,1,5,5,6,6-hepta fluoro-3-oxahexane, bp 60°–61° (15 mm, 2.0 kPa). IR (CCl$_4$): 3010, 2970, and 2660 (sat'd CH), 2150 (N$_3$), 1300–1100 cm$^{-1}$ (CF, C—O). NMR (CCl$_4$): $^1$H 4.10 (q, $J_{FF}$ 7.8 Hz, 2H, CH$_2$CF$_3$) and 3.67 ppm (s, 3H, OCH$_3$); $^{19}$F −73.8 (t of t, $J_{FF}$ 9.3, 7.9 Hz, 3F, CF$_3$), −75.3 (t, $J_{HF}$ 7.8 Hz, 3F, CF$_3$CH$_2$), −89.3 (q or t, $J_{FF}$ 7.9, 3.4 Hz, 2F, CF$_2$N$_3$), and 117.7 ppm (q of t, $J_{FF}$ 9.3, 3.4 Hz, CF$_2$).

Anal. Calcd for C$_7$H$_5$F$_{10}$N$_3$O$_2$: C, 23.81; H, 1.43; N, 11.90. Found: C, 23.89; H, 1.43; N, 12.00.

EXAMPLE 6

4-Azidoheptafluorobutanone-2

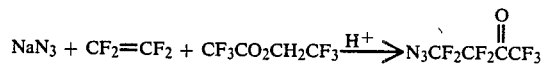

Sodium azide, trifluoroethyl trifluoroacetate and tetrafluorethylene were mixed and reacted, as in Example 6, at ambient temperature (exotherm to 34°) for 4 h and then at 50° for 1 h. After several weeks, the reaction mixture was stirred into a solution of 300 mL of concentrated HCl in 1 L of ice water. The mixture was extracted continuously with ether for one day. The extracts were distilled until the pot temperature reached 60°. The residue from the distillation was divided into portions. A 25 mL portion was added dropwise to 50 mL of concentrated H$_2$SO$_4$ at 10°, stirred for an additional 30 min and evacuated at 10 mm (1.3 kPa). To a 250 mL-portion, 600 mL of concentrated H$_2$SO$_4$ was added dropwise. The mixture was stirred for 1 h and then evacuated at 10 mm (1.3 kPa). The combined product was 83.7 g (88%) of 4-azidoheptafluorobutanone-2, pure by GC. IR (CCl$_4$): 2150 (N$_3$), 1790 (C=O), and 1250–1100 cm$^{-1}$ (CF). NMR (CCl$_4$): $^{19}$F −75.6 (t of t, $J_{FF}$ 8.3, 2.9 Hz, 3F, CF$_3$), −89.9 (m, 2F, CF$_2$N$_3$), and −120.8 (q of t, $J_{FF}$ 8.3, 4.5 Hz, 2F, CF$_2$C=O). An analytical sample was distilled from P$_2$O$_5$, bp 64°.

Anal. Calcd for C$_4$F$_7$N$_3$O: C, 20.10; N, 17.58. Found: C, 20.20; N, 17.59.

EXAMPLE 7

1-Azidononafluoropentanone-3

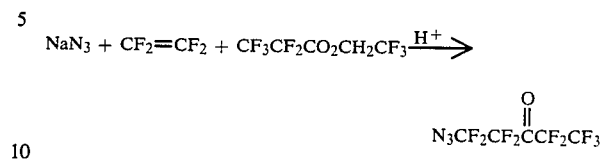

Trifluoroethyl pentafluoropropionate, bp 70°, was prepared in 79% yield by reaction of equimolar amounts of trifluoroethanol, pentafluoropropionyl chloride, and pyridine in diglyme. IR (CCl$_4$): 2970 (sat'd CH), 1800 (C=O), and 1300–1150 cm$^{-1}$ (CF, C—O).

A mixture of 26.0 g (0.40 mol) of sodium azide, 102 g (0.41 mol) of trifluoroethyl pentafluoropropionate, 150 mL of DMSO, and 40 g (0.40 mol) of tetrafluoroethylene was reacted in a 400-mL tube for 6 h at room temperature (22° to 34°). The reaction mixture was cooled and stirred while 57 g (0.50 mol) of trifluoroacetic acid was added. Then 25 mL of ether was added, and the whole heated slowly to 53° at 1.4 mm (0.2 kPa). Volatile product so obtained was diluted with 75 mL of ether and distilled until the head temperature reached 40°. The residue was cooled and stirred with 250 mL of concentrated H$_2$SO$_4$ for 2 h, then evacuated at 1.6 mm (0.2 kPa) at room temperature to give 102.1 g (88%) of 1-azidononafluoropentanone-3, nearly pure by GC. IR (CCl$_4$): 2140 (N$_3$), 1780 (C=O), and 1300–1100 cm$^{-1}$ (CF). NMR (CCl$_4$): $^{19}$F −82.4 (t, $J_{FF}$ 3.1 Hz, 3F, CF$_3$), −89.8 (p, $J_{FF}$ 4.5 Hz, 2F, CF$_2$N$_3$), −120.0 (m, 2F, CF$_2$), and −121.4 ppm (t of d of q, $J_{FF}$ 11.8, 4.5, 1 Hz, 2F, CF$_2$).

EXAMPLE 8

1-Methoxy-5-azidooctafluoropentanone-3

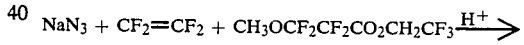

Trifluoroethyl 3-methoxytetrafluoropropionate was prepared by reaction of 97.3 g (0.50 mol) of 3-methoxytetrafluoropropionyl chloride, 55.0 g (0.55 mol) of trifluoroethanol, and 39.5 g (0.50 mol) of pyridine in 100 mL methylene chloride. Reaction was extremely slow until the pyridine was added. After having stirred overnight, the reaction mixture was filtered, solids were rinsed with methylene chloride, and filtrates were distilled to give 119.4 g of ester, bp 44°–49° (20 mm, 2.7 kPa). The cloudy product was treated with 2 g of P$_2$O$_5$ and filtered to afford 109.3 g (93%) of the desired ester, pure by GC. IR (CCl$_4$): 2855, 2975, and 3010 (sat'd CH), 1790 (C=O), and 1300–1100 cm$^{-1}$ (CF, C—O).

A 400-mL tube was charged with 26.0 g (0.40 mol) of sodium azide, 109 g (0.42 mol) of trifluoroethyl 3-methoxytetrafluoropropionate, 150 mL of DMSO, and 40 g (0.40 mol) of tetrafluoroethylene and was agitated at 24°–37° for 6 h, then at 40° for 2 h. The reaction mixture was poured into 300 mL of concentrated HCl and 1 L of water. A lower layer was separated and an aqueous layer was extracted with 250 mL, and then with 100 mL, of ether. The combined organic layers were washed with 100 mL of water, dried over CaSO$_4$, and distilled to afford 78.7 g (65%) of 1-azido-5-methoxyoctafluoropentanone-3, bp 62° (40 mm, 5.3 kPa). IR (CCl4): 3010, 2960, and 2860 (sat'd CH), 2145 (N3), 1775 (C=O), and 1250–1100 cm$^{-1}$ (CF, C—O). NMR (CCl4): $^1$H 3.72 ppm (s, CH3O); $^{19}$F −90.1 (p, $J_{FF}$4 Hz, 2F, CF2), −90.3 (p, $J_{FF}$4 Hz, 2F, CF2), −119.8 (m, 2F, CF2), and −210.8 ppm (m, 2F, CF2).

Anal. Calcd for C6H3F8N3O2: C, 23.93; H, 1.00; N, 13.96. Found: C, 23.77; H, 1.01; N, 13.89.

EXAMPLE 9

1,9-Bisazidododecafluoro-5-oxanonane-3,7-dione

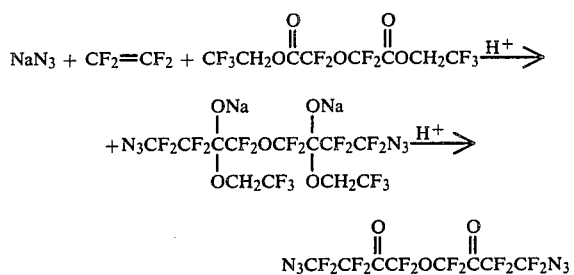

Crude tetrafluorodiglycolic acid hydrate (129 g, 0.6 mol), obtained by permanganate oxidation of 3,4-dichloro-2,2,5,5-tetrafluoro-2,5-dihydrofuran, was stirred with 130 g (1.3 mol) of trifluoroethanol and 200 mL of concentrated H2SO4 at 25° for 4 days. The upper layer was extracted with 25 mL of concentrated H2SO4, clarified with CaSO4, and distilled to give 130.8 g (59%) of bis(trifluoroethyl)tetrafluorodiglycolate, bp 85°–86° (20 mm, 2.7 kPa). IR (neat): 2985 (sat'd CH), 1810 (C=O), 1250–110 cm$^{-1}$ (CF, C—O). NMR (CCl4); $^1$H 4.63 ppm (q, $J_{HF}$7.8 Hz, CH2CF3); $^{19}$F −69.6 (t, $J_{HF}$7.8 Hz, 6F, CF3CH2) and −77.7 ppm (s, 4F, CF2O).

A 400-mL tube was charged with 66.6 g (0.18 mol) of bis(trifluoroethyl)tetrafluorodiglycolate, 11.7 g (0.18 mol) of sodium azide, 150 mL of DMSO, and 20 g (0.20 mol) of tetrafluoroethylene and was agitated at 25°–34° for 6 h, then at 40° for 2 h. The reaction mixture was poured into 300 mL of concentrated HCl in 1 L of water. A lower layer was removed and an aqueous phase was extracted with 2X 250 mL of ether. The combined organic layers were washed with 100 mL of water and dried over CaSO4. Distillation produced 5.5 g (13% based on NaN3) of 1,9-bisazidododecafluoro-5-oxanonane-3,7-dione, bp 45° (0.5 mm, 0.1 kPa). Analytical data indicated the presence of an impurity containing a CF3CH2O-group. IR (neat): 2160 (N3), 1790 (C=O), and 1300–1100 cm$^{-1}$ (CF, C—O). NMR (CD3CN): $^1$H traces —OCH2CF3; $^{19}$F −76.7 (m, 4F, CF2O), −89.1 (m, 4F, CF2N3), and −119.2 ppm (rough septet, $J_{FF}$4.5 Hz, 4F, CF2C=O).

Anal. Calcd for C8F12N6O3: C, 21.07; N, 18.43. Found: C, 20.75; N, 17.33.

EXAMPLE 10

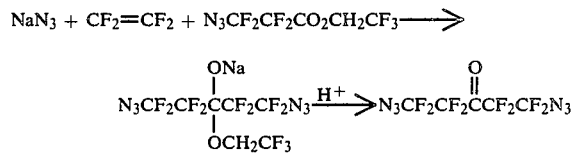

Trifluoroethyl 3-azidotetrafluoropropionate was prepared by treatment of methyl 3-azidotetrafluoropropionate with excess trifluoroethanol and concentrated H2SO4 at 25° for 4 days. Product, bp 58°–60° (50 mm, 6.7 kPa) was isolated in 55% yield by evaporation of volatiles from the sulfuric acid followed by fractionation. IR (CCl4): 2970 (sat'd CH), 2140 (N3), 1795 (C=O), and 1300–1100 cm$^{-1}$ (CF, C—O). NMR (CCl4): $^1$H 4.68 ppm (q, $J_{HF}$ 7.8 Hz, CH2CF3) with a small amount of N3 CF2CF2CO2CH3 indicated as impurity; $^{19}$F −74.8 (t, $J_{HF}$ 7.8 Hz, 3F, CF3CH2), −91.3 (t, $J_{FF}$4.7 Hz, 2F, CF2N3), and −120.8 ppm (t, $J_{FF}$4.7 Hz, 2F, CF2C=O).

Anal. Calcd for C5H2F7N3O2: C, 22.32; H, 0.75; N, 15.62. Found: C, 22.57; H, 0.95; N, 16.24.

A 400-mL tube was charged with 49.4 g (0.18 mol) of trifluoroethyl 3-azidotetrafluoropropionate, 150 mL of DMSO, 12.0 g (0.18 mol) of sodium azide, and 18 g (0.18 mol) of tetrafluoroethylene and was agitated at 25° for 6 h, then at 40° for 2 h. The reaction mixture was poured into 250 mL of concentrated HCl in 1 L of water. The resulting mixture was extracted with 4×200 mL of ether, the combined ether solutions were washed with 500 mL of water, dried over P2O5, and the ether was distilled off. Product was removed from the residue under vacuum, dried over CaSO4 and fractionated to afford 20.5 g (39%) of 1,5-bisazidooctafluoropentanone-3, bp 50°–51° (25 mm, 3.3 kPa). IR (CCl4): 2140 (N3), 1770 (C=O), and 1300–1100 cm$^{-1}$ (CF). NMR (CCl4): $^{19}$F −89.8 (s, 2F, CF2N3) and −119.9 ppm (s, 2F, CF2=O). Mass spec (C.I.): m/e 293 (M$^+$—F), 265 (M$^+$—F—N2), 237 (M$^+$—F—2N2), 170 (N3CF2CF2CO$^+$), 142 (N3CF2CF]2$^+$), 114 (C2F4N$^+$), 100 (C2F4$^+$), 92 (N3CF2$^+$) with other unexplained bands present.

Anal. Calcd for C5F8N6O: C, 19.24; N, 26.93. Found: C, 19.22; N, 25.97.

EXAMPLE 11

4-Methylsulfonylheptafluorobutanone-2

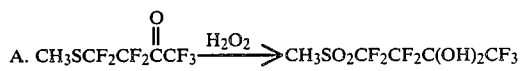

A solution of 26.8 g (0.11 mol) of 4-methylthioheptafluorobutanone-2 in 25 mL of acetic acid was stirred at 90° while a mixture of 23.0 mL (25.5 g, 0.23 mol) of 30% hydrogen peroxide and 20 mL of acetic acid was added over 30 min. The mixture was stirred at 90°–95° for an additional 3 h and distilled to give 22.9 g (71%) of 4-methylsulfonylheptafluorobutanone-2 hydrate, bp 98°–100° (50 mm, 6.7 kPa). IR (neat): 3440 (broad, OH), 2940(sat'd CH), 1350 (SO2), and 1250–1050 cm$^{-1}$ (CF, CO, SO2). NMR (acetone-d6): $^1$H 7.71 (broad s, 2H, OH) and 3.26 ppm (s, 3H, CH3SO2); $^{19}$F −81.2 (t of t, $J_{FF}$ 10.8, 5 Hz, 3F, CF3), −112.7 (m, 2F, CF2), and −119.2 ppm (m, 2F, CF2).

Anal. Calcd for C5H5F7O4S: C, 20.42; H, 1.71 Found: C, 20.86; H, 2.19.

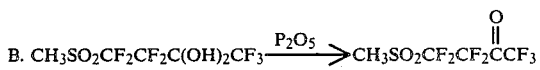

4-Methylsulfonylheptafluorobutanone-2 hydrate (17.4 g, 0.059 mol) was added to 31.2 g (0.20 mol) of P2O5 and heated to 100°. Distillation then gave 13.3 g (82%) of 4-methylsulfonylheptafluorobutanone-2, bp 85°–110° (100 mm, 13.3 kPa). IR (CCl$_4$): 3040, 3020, and 2940 (sat'd CH), 1790 (C=O), 1370 (SO$_2$), and 1300–1100 (CF, SO$_2$). NMR (CD$_3$CN): $^1$H 3.27 ppm (t of t, J$_{HF}$ 1.8, 0.5 Hz, CH$_3$SO$_2$); $^{19}$F −74.3 (t of t, J$_{FF}$ 8.4, 3.5 Hz, 3F, CF$_3$), −114.8 (m, 2F, CF$_2$SO$_2$), and −117.4 ppm (q of t, J$_{FF}$ 8.4, 4.2 Hz, 2F, CF$_2$C=O).

Anal. Calcd for C$_5$H$_3$F$_7$O$_3$S: C, 21.75; H, 1.09. Found: C, 21.84; H, 1.46.

EXAMPLE 12

9-Azido-perfluoro-2,5,7,-trimethyl-3,6-dioxananoyl Fluoride

A. N$_3$CF$_2$CF$_2$CCF$_3$ + CF$_3$CF——CF$_2$ $\xrightarrow{KF}$

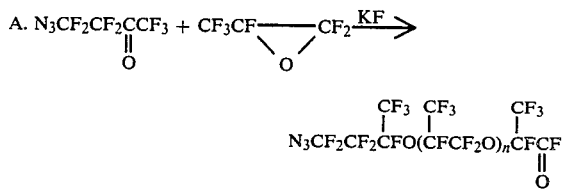

A suspension of 4.0 g (0.068 mol) of flame-dried KF in 400 mL of tetraglyme was stirred at 25° while a solution of 79.0 g (0.33 mol) of 4-azidoheptafluorobutanone-2 in 100 mL of tetraglyme was added. The mixture was further stirred at 15°–25° while 113 g (0.68 mol) of HFPO was distilled in over a 5 h period. The mixture was stirred, until condensation in a −80° condenser ceasred, and then heated under vacuum to 50° (0.1 mm, 0 kPa) while 126.3 g of volatiles was removed. Fractionation gave 47.4 g (35%) of crude 1:1 adduct, bp 58°–62° (80 mm, 10.7 kPa), and 50.5 g (27%) of 2:1 adduct, perfluoro (9-azido-2,5,7-trimethyl-3,6-dioxanonanoyl)fluoride, bp 58°–59° (8 mm, 1.1 kPa). For the 2:1 adduct, IR (CCl$_4$): 2150 (N$_3$), 1880 (COF), 1300–110 cm$^{-1}$ (CF, C—O). NMR (CCl$_4$): $^{19}$F fits a mixture of racemates of N$_3$CF$_2$CF$_2$CF(CF$_3$)OCF(CF$_3$)CF$_2$OCF(CF$_3$)COF.

Anal. Calcd for C$_{10}$F$_{19}$N$_3$O$_3$: C, 21.03; N, 7.36. Found: C, 21.12; N, 7.84.

Washing of the high-boiling residue from evaporation of volatile products and distillation of water-insoluble product gave 25.0 g (10%) of 3:1 adduct as the carboxylic acid, bp 56°–58° (0.03 mm, 0 kPa).

B. 9-Azido-perfluoro-5,7-dimethyl-3,6-dioxanonene-1

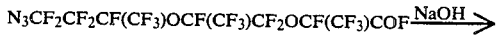

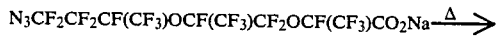

A 22.8 g (0.04 mol) sample of the above 2:1 adduct was stirred with 75 mL of water and a few drops of phenolphthalein while aqueous NaOH solution was added dropwise to a permanent endpoint. Most of the water was then evaporated in a stream of air, and a residual moist cake was dried by heating it slowly to 140° (0.1 mm, 0 kPa). Further heating of the dry salt to 220° caused the pressure to rise to 1.8 mm (0.2 kPa). The pyrolysis was carried out at 220°–223° until the pressure dropped to 0.3 mm (0 kPa) after 12 h. The crude product, 16.9 g, was dried and distilled to afford 8.0 g (40%) of perfluoro (9-azido-5,7-dimethyl-3,6-dioxanonene-1), bp 64°–66° (20 mm, 2.7 kPa), only very minor impurities by GC. IR (neat): 2150 (N$_3$), 1840 (C=C), 1300–1100 cm$^{-1}$ (CF, CO). NMR (CCl$_4$): $^{19}$F compatible with N$_3$CF$_2$CF$_2$CF(CF$_3$)OCF(CF$_3$)CF$_2$OCF=CF$_2$.

Anal. Calcd for C$_9$F$_{17}$N$_3$O$_2$: C, 21.40; N, 8.32. Found: C, 21.58; N, 8148.

C. N$_3$CF$_2$CF$_2$CF(CF$_3$)OCF(CF$_3$)CF$_2$OCF=CF$_2$ + CF$_2$=CF$_2$

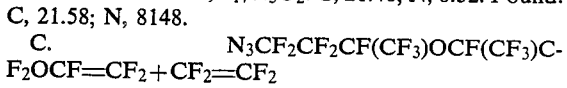

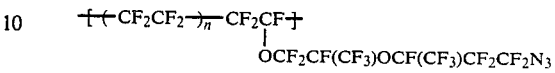

A mixture of 16.7 g (0.033 mol) of the above trifluorovinyl ether, 20 mL of CFCl$_2$CF$_2$Cl, and 2 mL of 3% perfluoropropionyl peroxide in CFCl$_2$Cl was shaken in a 100 mL stainless steel-lined tube at 25°–30° with about 200 psi (1.4 MPa) of tetrafluoroethylene. The tube was repressured with tetrafluoroethylene as needed until 30 g (0.30 mol) had been added. The reaction was continued for an additional 1.5 h. A moist solid polymer which was produced was dried to constant weight under vacuum to give 16.1 g white solid copolymer. IR (nujol): 2160 (N$_3$) and 1250–1150 cm$^{-1}$ (CF, C—O).

EXAMPLE 13

7-Methylsulfonylperfluoro-5-methyl-4-oxaheptene-1

CH$_3$SO$_2$CF$_2$CF$_2$CCF$_3$ + KF + CF$_2$=CFCF$_2$OSO$_2$F ⟶

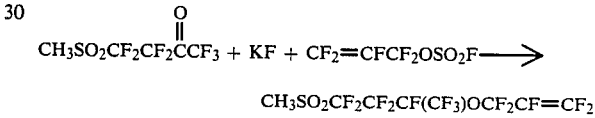

CH$_3$SO$_2$CF$_2$CF$_2$CF(CF$_3$)OCF$_2$CF=CF$_2$

A mixture of 12.76 g (0.046 mol) of 4-methylsulfonyl-heptafluorobutanone-2, 2.91 g (0.05 mol) of flame-dried KF, and 100 mL of diglyme was stirred for 15 min. Stirring was continued at 0°–5° while 10.6 g (0.046 mol) of perfluoroallyl fluorosulfate was added dropwise. The mixture was stirred at 0°–5° for another 2 h and then poured into 500 mL of cold water. The lower layer was washed with 100 mL of water, dried over CaSO$_4$, and fractionated to give 4.3 g (22%) of 7-methylsulfonyl-5-trifluoromethyl-4-oxadecafluoroheptene-1, bp 83° (1.9 mm, 0.3 kPa). IR (neat): 3040, 3020, and 2930 (sat'd CH), 1790 (C=C), 1380 (SO$_2$), and 1250–110 cm$^{-1}$ (CF, C—O). Proton and $^{19}$F NMR spectra support the assigned structure.

Anal. Calcd for C$_8$H$_3$F$_{13}$O$_3$S: C, 22.55; H, 0.71. Found: C, 22.26; H, 0.84.

I claim:

1. The β-substituted polyfluoroethyl compound having the formula, XCF$_2$CFYZ, wherein
   X is —SR$^1$ and —SO$_2$R$^1$;
   Y is —F, —Cl or —OR$_F{^1}$;
   Z is —C(O)R$_F$X$^1$;
   R$^1$ is C$_1$ to $_{10}$ alkyl, C$_6$ to $_{10}$ aryl, or C$_6$ to $_{10}$ aralkyl;
   R$_F{^1}$ is C$_1$ to $_4$ perfluoroalkyl;
   R$_F$ is —CF$_2$—, C$_2$ to $_8$ perfluoroalkylene, or C$_2$ to $_8$ perfluoroalkylene containing one in-chain ether oxygen bond, or two in-chain ether oxygen bonds separated by at least two carbon atoms;
   X$^1$ is —F or —OR$^2$; and
   R$^2$ is —CH$_3$, —C$_2$H$_5$ or phenyl.

2. The compound of claim 1 wherein X is SR$^1$.

3. The compound of claim 2 wherein X$^1$ is —F or —OCH$_3$ and Y is —F or —OCF$_3$.

4. The compound of claim 3 wherein $R_F$ is $-CF_2-$, $-CF_2CF_2-$ or $-CF_2OCF_2-$ and $R^1$ is $-CH_3$, $-C_2H_5$ or phenyl.

5. The compound of claim 4 wherein $X^1$ is $-F$.

6. The compound of claim 4 wherein $X^1$ is $-OCH_3$.

7. The compound of claim 1 wherein
X is $-SCH_3$ or $-SO_2CH_3$;
Y is $-F$ or $-OCF_3$; and
Z is selected from $-COCF_3$, $-COC_2F_5$, and $-COCF_2CF_2OCH_3$.

8. The compound of claim 7 wherein X is $-SO_2CH_3$.

9. The compound of claim 7 wherein Z is $-COCF_3$.

10. The compound of claim 7 wherein Z is $-COC_2F_5$.

11. The compound of claim 7 wherein Z is $-COCF_2CF_2OCH_3$.

12. The compound of claim 8 wherein Z is $-COCF_3$.

13. The compound of claim 7 wherein X is $-SCH_3$.

14. The compound of claim 13 wherein Z is $-COCF_3$ or $-COCF_2CF_2OCH_3$.

* * * * *